(12) United States Patent
Knapp et al.

(10) Patent No.: US 8,998,882 B2
(45) Date of Patent: Apr. 7, 2015

(54) ENHANCED PRE-WETTED INTERMITTENT CATHETER WITH LUBRICIOUS COATING

(71) Applicant: C. R. Bard, Inc., Murray Hill, NJ (US)

(72) Inventors: Tracey E. Knapp, Lawrenceville, GA (US); Vasu Nishtala, Plano, TX (US)

(73) Assignee: C. R. Bard, Inc., Murray Hill, NJ (US)

( * ) Notice: Subject to any disclaimer, the term of this patent is extended or adjusted under 35 U.S.C. 154(b) by 94 days.

(21) Appl. No.: 13/802,095

(22) Filed: Mar. 13, 2013

(65) Prior Publication Data
US 2014/0262859 A1 Sep. 18, 2014

(51) Int. Cl.
| | |
|---|---|
| *A61M 25/00* | (2006.01) |
| *A61M 25/01* | (2006.01) |
| *A61M 27/00* | (2006.01) |
| *B65D 85/04* | (2006.01) |
| *B65D 85/675* | (2006.01) |
| *A61M 25/06* | (2006.01) |
| *B65D 85/671* | (2006.01) |

(52) U.S. Cl.
CPC ..... *A61M 25/002* (2013.01); *A61M 2025/0681* (2013.01); *A61M 25/0111* (2013.01); *A61M 25/0017* (2013.01); *A61M 2210/1089* (2013.01); *A61M 27/008* (2013.01); *B65D 85/671* (2013.01); *A61M 2210/1085* (2013.01); *B65D 85/04* (2013.01); *A61M 2210/1078* (2013.01); *B65D 85/675* (2013.01); *A61M 25/0113* (2013.01); *A61M 2202/0496* (2013.01)

(58) Field of Classification Search
CPC ............ A61M 25/0111; A61M 25/0017; A61M 25/002; A61M 2025/0681; A61M 25/0113; A61M 27/008; A61M 2210/1078; A61M 2210/1082; A61M 2210/1085; A61M 2210/1089; A61M 2202/0496; B65D 85/671; B65D 85/675; B65D 85/04
See application file for complete search history.

(56) References Cited

U.S. PATENT DOCUMENTS

| | | | |
|---|---|---|---|
| 1,888,349 | A | 11/1932 | Jacoby |
| 2,912,981 | A | 11/1959 | Keough |
| 2,919,697 | A | 1/1960 | Kim |
| 3,173,566 | A | 3/1965 | Talbert |
| 3,344,791 | A | 10/1967 | Foderick |
| 3,556,294 | A | 1/1971 | Walck et al. |
| 3,556,874 | A | 1/1971 | McClain |

(Continued)

FOREIGN PATENT DOCUMENTS

| | | |
|---|---|---|
| CN | 102939127 A | 2/2013 |
| DE | 10213411 A1 | 10/2003 |

(Continued)

OTHER PUBLICATIONS

CA 2,769,026 filed Jan. 24, 2012 First Examination Report dated Nov. 4, 2013.

(Continued)

*Primary Examiner* — Adam Marcetich
(74) *Attorney, Agent, or Firm* — Rutan & Tucker, LLP

(57) ABSTRACT

The present disclosure relates to a packaged urinary catheter. The catheter includes a conduit having a proximal end and a distal end. The distal end includes at least one aperture for receiving urine from the bladder. The catheter is contained within a sleeve having a length, a width, and a size configured to receive the catheter. According to one embodiment, the catheter and the sleeve may be arranged in a helical coil. The outer surface of the catheter may have a lubricious and/or an antimicrobial coating.

20 Claims, 6 Drawing Sheets

(56) References Cited

U.S. PATENT DOCUMENTS

| | | | |
|---|---|---|---|
| 3,566,874 A | 3/1971 | Shepherd et al. | |
| 3,648,704 A | 3/1972 | Jackson | |
| 3,695,921 A | 10/1972 | Shepard et al. | |
| 3,699,964 A | 10/1972 | Ericson | |
| 3,726,281 A | 4/1973 | Norton et al. | |
| 3,794,042 A | 2/1974 | De Klotz et al. | |
| 3,802,987 A * | 4/1974 | Noll | 156/296 |
| 3,835,992 A * | 9/1974 | Adams, IV | 206/390 |
| 3,854,483 A | 12/1974 | Powers | |
| 3,861,395 A | 1/1975 | Taniguchi | |
| 3,898,993 A | 8/1975 | Taniguchi | |
| 3,934,721 A | 1/1976 | Juster et al. | |
| 3,967,728 A | 7/1976 | Gordon et al. | |
| 4,026,296 A | 5/1977 | Stoy et al. | |
| 4,055,682 A | 10/1977 | Merrill | |
| 4,062,363 A | 12/1977 | Bonner, Jr. | |
| 4,069,359 A * | 1/1978 | DeMarse et al. | 428/36.5 |
| 4,091,922 A | 5/1978 | Egler | |
| 4,140,127 A | 2/1979 | Cianci et al. | |
| 4,198,983 A | 4/1980 | Becker et al. | |
| 4,230,115 A | 10/1980 | Walz, Jr. et al. | |
| 4,245,639 A | 1/1981 | La Rosa | |
| 4,246,909 A | 1/1981 | Wu et al. | |
| 4,269,310 A | 5/1981 | Uson | |
| 4,306,557 A | 12/1981 | North | |
| 4,350,161 A | 9/1982 | Davis, Jr. | |
| 4,366,901 A | 1/1983 | Short | |
| 4,392,848 A | 7/1983 | Lucas et al. | |
| 4,411,648 A | 10/1983 | Davis et al. | |
| 4,515,593 A | 5/1985 | Norton | |
| 4,517,971 A | 5/1985 | Sorbonne | |
| 4,560,382 A | 12/1985 | Isono et al. | |
| 4,571,241 A | 2/1986 | Christopher | |
| 4,585,666 A | 4/1986 | Lambert | |
| 4,597,765 A | 7/1986 | Klatt | |
| 4,607,746 A * | 8/1986 | Stinnette | 206/53 |
| 4,610,670 A | 9/1986 | Spencer | |
| 4,619,642 A | 10/1986 | Spencer | |
| 4,681,572 A | 7/1987 | Tokarz et al. | |
| 4,692,154 A | 9/1987 | Singery et al. | |
| 4,696,672 A | 9/1987 | Mochizuki et al. | |
| 4,704,102 A | 11/1987 | Guthery | |
| 4,723,946 A | 2/1988 | Kay | |
| 4,738,667 A | 4/1988 | Galloway | |
| 4,754,877 A | 7/1988 | Johansson et al. | |
| 4,759,753 A | 7/1988 | Schneider et al. | |
| 4,762,128 A | 8/1988 | Rosenbluth | |
| 4,773,901 A | 9/1988 | Norton | |
| 4,784,651 A | 11/1988 | Hickey et al. | |
| 4,811,847 A | 3/1989 | Reif et al. | |
| 4,838,876 A | 6/1989 | Wong et al. | |
| 4,886,508 A | 12/1989 | Washington | |
| 4,888,005 A | 12/1989 | Dingeman et al. | |
| 4,893,623 A | 1/1990 | Rosenbluth | |
| 4,932,938 A | 6/1990 | Goldberg et al. | |
| 4,957,487 A | 9/1990 | Gerow | |
| 4,997,426 A | 3/1991 | Dingeman et al. | |
| 5,007,897 A | 4/1991 | Kalb et al. | |
| 5,045,078 A | 9/1991 | Asta | |
| 5,077,352 A | 12/1991 | Elton | |
| 5,087,252 A | 2/1992 | Denard | |
| 5,098,379 A | 3/1992 | Conway et al. | |
| 5,100,396 A | 3/1992 | Zamierowski | |
| 5,137,671 A | 8/1992 | Conway et al. | |
| 5,147,341 A | 9/1992 | Starke et al. | |
| 5,174,290 A | 12/1992 | Fiddian-Green | |
| 5,179,174 A | 1/1993 | Elton | |
| 5,180,591 A | 1/1993 | Magruder et al. | |
| 5,186,172 A | 2/1993 | Fiddian-Green | |
| 5,188,596 A | 2/1993 | Condon et al. | |
| 5,201,724 A | 4/1993 | Hukins et al. | |
| 5,209,726 A | 5/1993 | Goosen | |
| 5,209,728 A | 5/1993 | Kraus et al. | |
| 5,224,953 A | 7/1993 | Morgentaler | |
| 5,226,530 A | 7/1993 | Golden | |
| 5,234,411 A | 8/1993 | Vaillancourt | |
| 5,236,422 A | 8/1993 | Eplett, Jr. | |
| 5,242,428 A | 9/1993 | Palestrant | |
| 5,261,896 A | 11/1993 | Conway et al. | |
| 5,269,755 A | 12/1993 | Bodicky | |
| 5,269,770 A | 12/1993 | Conway et al. | |
| 5,282,795 A | 2/1994 | Finney | |
| 5,352,182 A | 10/1994 | Kalb et al. | |
| 5,360,402 A | 11/1994 | Conway et al. | |
| 5,370,899 A | 12/1994 | Conway et al. | |
| 5,415,165 A | 5/1995 | Fiddian-Green | |
| 5,417,666 A | 5/1995 | Coulter | |
| 5,433,713 A | 7/1995 | Trotta | |
| 5,445,626 A | 8/1995 | Gigante et al. | |
| 5,447,231 A | 9/1995 | Kastenhofer | |
| 5,454,798 A | 10/1995 | Kubalak et al. | |
| 5,456,251 A | 10/1995 | Fiddian-Green | |
| 5,466,229 A | 11/1995 | Elson et al. | |
| 5,476,434 A | 12/1995 | Kalb et al. | |
| 5,482,740 A | 1/1996 | Conway et al. | |
| 5,501,669 A | 3/1996 | Conway et al. | |
| 5,509,889 A | 4/1996 | Kalb et al. | |
| 5,514,112 A | 5/1996 | Chu et al. | |
| 5,520,636 A | 5/1996 | Korth et al. | |
| 5,531,715 A | 7/1996 | Engelson et al. | |
| 5,531,717 A | 7/1996 | Roberto et al. | |
| 5,536,258 A | 7/1996 | Folden | |
| 5,558,900 A | 9/1996 | Fan et al. | |
| 5,569,219 A | 10/1996 | Hakki et al. | |
| 5,582,599 A | 12/1996 | Daneshvar | |
| 5,591,292 A * | 1/1997 | Blomqvist | 156/244.13 |
| 5,599,321 A | 2/1997 | Conway et al. | |
| 5,601,537 A | 2/1997 | Frassica | |
| 5,607,417 A | 3/1997 | Batich et al. | |
| 5,616,126 A | 4/1997 | Malekmehr et al. | |
| 5,624,395 A | 4/1997 | Mikhail et al. | |
| 5,653,700 A | 8/1997 | Byrne et al. | |
| 5,670,111 A | 9/1997 | Conway et al. | |
| 5,688,516 A | 11/1997 | Raad et al. | |
| 5,704,353 A | 1/1998 | Kalb et al. | |
| 5,707,357 A | 1/1998 | Mikhail et al. | |
| 5,711,841 A | 1/1998 | Jaker | |
| 5,749,826 A | 5/1998 | Faulkner | |
| 5,779,670 A | 7/1998 | Bidwell et al. | |
| 5,782,808 A | 7/1998 | Folden | |
| 5,785,694 A | 7/1998 | Cohen et al. | |
| 5,788,687 A | 8/1998 | Batich et al. | |
| 5,800,339 A | 9/1998 | Salama | |
| 5,817,067 A | 10/1998 | Tsukada et al. | |
| 5,820,583 A | 10/1998 | Demopulos et al. | |
| 5,840,151 A * | 11/1998 | Munsch | 156/380.2 |
| 5,853,518 A | 12/1998 | Utas et al. | |
| 5,871,475 A | 2/1999 | Frassica | |
| 5,895,374 A | 4/1999 | Rodsten et al. | |
| 5,897,535 A | 4/1999 | Feliziani et al. | |
| 5,941,856 A | 8/1999 | Kovacs et al. | |
| 5,971,954 A | 10/1999 | Conway et al. | |
| 5,980,483 A | 11/1999 | Dimitri et al. | |
| 5,989,230 A | 11/1999 | Frassica | |
| 6,004,305 A | 12/1999 | Hursman et al. | |
| 6,007,521 A | 12/1999 | Bidwell et al. | |
| 6,024,751 A | 2/2000 | Lovato et al. | |
| 6,050,934 A | 4/2000 | Mikhail et al. | |
| 6,053,905 A | 4/2000 | Daignault, Jr. et al. | |
| 6,056,715 A | 5/2000 | Demopulos et al. | |
| 6,059,107 A | 5/2000 | Nosted et al. | |
| 6,063,063 A | 5/2000 | Harboe et al. | |
| 6,090,075 A | 7/2000 | House | |
| 6,156,049 A | 12/2000 | Lovato et al. | |
| 6,162,201 A | 12/2000 | Cohen et al. | |
| 6,183,461 B1 | 2/2001 | Matsuura et al. | |
| 6,186,990 B1 | 2/2001 | Chen et al. | |
| 6,190,353 B1 | 2/2001 | Makower et al. | |
| 6,210,394 B1 | 4/2001 | Demopulos et al. | |
| 6,221,056 B1 | 4/2001 | Silverman | |
| 6,238,383 B1 | 5/2001 | Karram et al. | |
| 6,254,570 B1 | 7/2001 | Rutner et al. | |
| 6,254,582 B1 * | 7/2001 | O'Donnell et al. | 604/385.05 |
| 6,254,585 B1 | 7/2001 | Demopulos et al. | |

(56) References Cited

U.S. PATENT DOCUMENTS

| | | |
|---|---|---|
| 6,261,279 B1 | 7/2001 | Demopulos et al. |
| 6,293,923 B1 | 9/2001 | Yachia et al. |
| 6,299,598 B1 | 10/2001 | Bander |
| 6,306,422 B1 | 10/2001 | Batich et al. |
| 6,329,488 B1 | 12/2001 | Terry et al. |
| 6,340,359 B1 | 1/2002 | Silverman |
| 6,355,004 B1 | 3/2002 | Pedersen et al. |
| 6,358,229 B1 | 3/2002 | Tihon |
| 6,368,315 B1 | 4/2002 | Gillis et al. |
| 6,368,317 B2 | 4/2002 | Chang |
| 6,379,334 B1 | 4/2002 | Frassica |
| 6,383,434 B2 | 5/2002 | Conway et al. |
| 6,391,010 B1 | 5/2002 | Wilcox |
| 6,391,014 B1 | 5/2002 | Silverman |
| 6,398,718 B1 | 6/2002 | Yachia et al. |
| 6,402,726 B1 | 6/2002 | Genese |
| 6,409,717 B1 | 6/2002 | Israelsson et al. |
| 6,458,867 B1 | 10/2002 | Wang et al. |
| 6,468,245 B2 | 10/2002 | Alexandersen et al. |
| 6,485,476 B1 | 11/2002 | von Dyck et al. |
| 6,544,240 B1 | 4/2003 | Borodulin et al. |
| 6,578,709 B1 | 6/2003 | Kavanagh et al. |
| 6,582,401 B1 | 6/2003 | Windheuser et al. |
| 6,602,244 B2 | 8/2003 | Kavanagh et al. |
| 6,613,342 B2 | 9/2003 | Aoki |
| 6,626,888 B1 | 9/2003 | Conway et al. |
| 6,629,969 B2 | 10/2003 | Chan et al. |
| 6,634,498 B2 | 10/2003 | Kayerod et al. |
| 6,638,269 B2 | 10/2003 | Wilcox |
| 6,648,906 B2 | 11/2003 | Lasheras et al. |
| 6,659,937 B2 | 12/2003 | Polsky et al. |
| 6,682,555 B2 | 1/2004 | Cioanta et al. |
| 6,695,831 B1 | 2/2004 | Tsukada et al. |
| 6,711,436 B1 | 3/2004 | Duhaylongsod |
| 6,716,895 B1 | 4/2004 | Terry |
| 6,719,709 B2 | 4/2004 | Whalen et al. |
| 6,730,113 B2 | 5/2004 | Eckhardt et al. |
| 6,736,805 B2 | 5/2004 | Israelsson et al. |
| 6,746,421 B2 | 6/2004 | Yachia et al. |
| 6,783,520 B1 | 8/2004 | Candray et al. |
| D496,266 S | 9/2004 | Nestenborg |
| 6,824,532 B2 | 11/2004 | Gillis et al. |
| 6,835,183 B2 | 12/2004 | Lennox et al. |
| 6,840,379 B2 | 1/2005 | Franks-Farah et al. |
| 6,848,574 B1 | 2/2005 | Israelsson et al. |
| 6,849,070 B1 | 2/2005 | Hansen et al. |
| 6,852,105 B2 | 2/2005 | Bolmsjo et al. |
| D503,335 S | 3/2005 | Risberg et al. |
| 6,869,416 B2 | 3/2005 | Windheuser et al. |
| 6,887,230 B2 | 5/2005 | Kubalak et al. |
| 6,889,740 B1 * | 5/2005 | Globensky et al. ............ 156/500 |
| 6,918,924 B2 | 7/2005 | Lasheras et al. |
| 6,926,708 B1 | 8/2005 | Franks-Farah et al. |
| 6,939,339 B1 | 9/2005 | Axexandersen et al. |
| 6,941,171 B2 | 9/2005 | Mann et al. |
| 6,942,634 B2 | 9/2005 | Odland |
| 6,945,957 B2 | 9/2005 | Freyman |
| 6,949,598 B2 | 9/2005 | Terry |
| 7,001,370 B2 | 2/2006 | Kubalak et al. |
| 7,048,717 B1 | 5/2006 | Frassica |
| 7,059,330 B1 | 6/2006 | Makower et al. |
| 7,066,912 B2 | 6/2006 | Nestenborg et al. |
| 7,087,041 B2 | 8/2006 | von Dyck et al. |
| 7,087,048 B1 | 8/2006 | Israelsson et al. |
| 7,094,220 B2 | 8/2006 | Tanghoj et al. |
| 7,160,277 B2 | 1/2007 | Elson et al. |
| 7,166,092 B2 | 1/2007 | Elson et al. |
| 7,195,608 B2 | 3/2007 | Burnett |
| 7,244,242 B2 | 7/2007 | Freyman |
| 7,250,043 B2 | 7/2007 | Chan et al. |
| 7,255,687 B2 | 8/2007 | Huang et al. |
| 7,270,647 B2 | 9/2007 | Karpowicz et al. |
| 7,294,117 B2 | 11/2007 | Provost-tine et al. |
| 7,311,690 B2 | 12/2007 | Burnett |
| 7,311,698 B2 | 12/2007 | Tanghoj et al. |
| 7,331,948 B2 | 2/2008 | Skarda |
| 7,334,679 B2 | 2/2008 | Givens, Jr. |
| 7,374,040 B2 | 5/2008 | Lee et al. |
| 7,380,658 B2 | 6/2008 | Murray et al. |
| 7,445,812 B2 | 11/2008 | Schmidt et al. |
| 7,458,964 B2 | 12/2008 | Mosler et al. |
| 7,476,223 B2 | 1/2009 | McBride |
| 7,507,229 B2 | 3/2009 | Hewitt et al. |
| 7,517,343 B2 | 4/2009 | Tanghoj et al. |
| 7,537,589 B2 | 5/2009 | Tsukada et al. |
| 7,571,804 B2 | 8/2009 | Kjellmann Bruun et al. |
| 7,601,158 B2 | 10/2009 | House |
| 7,615,045 B2 | 11/2009 | Israelsson et al. |
| 7,628,784 B2 | 12/2009 | Diaz et al. |
| 7,632,256 B2 | 12/2009 | Mosler et al. |
| 7,662,146 B2 | 2/2010 | House |
| 7,682,353 B2 | 3/2010 | Tanghoj et al. |
| 7,770,726 B2 | 8/2010 | Murray et al. |
| 7,789,873 B2 | 9/2010 | Kubalak et al. |
| 7,823,722 B2 | 11/2010 | Bezou et al. |
| 7,846,133 B2 | 12/2010 | Windheuser et al. |
| 7,938,838 B2 | 5/2011 | House |
| 7,947,021 B2 | 5/2011 | Bourne et al. |
| 7,985,217 B2 | 7/2011 | Mosler et al. |
| 8,011,505 B2 | 9/2011 | Murray et al. |
| 8,051,981 B2 | 11/2011 | Murray et al. |
| 8,066,693 B2 | 11/2011 | Tanghoj et al. |
| 8,177,774 B2 | 5/2012 | House |
| 8,181,778 B1 | 5/2012 | Van Groningen et al. |
| 8,205,745 B2 | 6/2012 | Murray et al. |
| 8,328,792 B2 | 12/2012 | Nishtala et al. |
| 8,454,569 B2 | 6/2013 | Kull-Osterlin et al. |
| 8,459,455 B2 | 6/2013 | Frojd |
| 8,475,434 B2 | 7/2013 | Frojd |
| 2001/0001443 A1 | 5/2001 | Kayerod et al. |
| 2001/0031952 A1 | 10/2001 | Karram et al. |
| 2001/0047147 A1 | 11/2001 | Slepian et al. |
| 2001/0054562 A1 | 12/2001 | Pettersson et al. |
| 2002/0007175 A1 | 1/2002 | Chang |
| 2002/0045855 A1 | 4/2002 | Frassica |
| 2002/0055730 A1 | 5/2002 | Yachia et al. |
| 2002/0077611 A1 | 6/2002 | von Dyck et al. |
| 2002/0082551 A1 | 6/2002 | Yachia et al. |
| 2002/0087131 A1 | 7/2002 | Wolff et al. |
| 2002/0094322 A1 | 7/2002 | Lawson et al. |
| 2002/0095133 A1 | 7/2002 | Gillis et al. |
| 2002/0099356 A1 | 7/2002 | Unger et al. |
| 2002/0103467 A1 | 8/2002 | Kubalak |
| 2002/0107467 A1 | 8/2002 | Levin |
| 2002/0156440 A1 | 10/2002 | Israelsson et al. |
| 2002/0165427 A1 | 11/2002 | Yachia et al. |
| 2003/0004496 A1 | 1/2003 | Tanghoj |
| 2003/0018293 A1 | 1/2003 | Tanghoj et al. |
| 2003/0018302 A1 | 1/2003 | Kavanagh et al. |
| 2003/0018322 A1 | 1/2003 | Tanghoj et al. |
| 2003/0028174 A1 | 2/2003 | Chan et al. |
| 2003/0036802 A1 | 2/2003 | Lennox et al. |
| 2003/0055403 A1 | 3/2003 | Nestenborg et al. |
| 2003/0060807 A1 | 3/2003 | Tanghoj et al. |
| 2003/0065292 A1 | 4/2003 | Darouiche et al. |
| 2003/0130646 A1 | 7/2003 | Kubalak et al. |
| 2003/0132307 A1 | 7/2003 | Park |
| 2003/0135200 A1 | 7/2003 | Byrne |
| 2003/0163079 A1 | 8/2003 | Burnett |
| 2003/0195478 A1 | 10/2003 | Russo |
| 2003/0225392 A1 | 12/2003 | McMichael et al. |
| 2003/0233084 A1 | 12/2003 | Slepian et al. |
| 2004/0030301 A1 | 2/2004 | Hunter |
| 2004/0034329 A1 | 2/2004 | Mankus et al. |
| 2004/0044307 A1 | 3/2004 | Richardson et al. |
| 2004/0049152 A1 | 3/2004 | Nayak |
| 2004/0049170 A1 | 3/2004 | Snell |
| 2004/0055925 A1 | 3/2004 | Franks-Farah et al. |
| 2004/0059280 A1 | 3/2004 | Makower et al. |
| 2004/0068251 A1 | 4/2004 | Chan et al. |
| 2004/0074794 A1 | 4/2004 | Conway et al. |
| 2004/0116551 A1 | 6/2004 | Terry |
| 2004/0127848 A1 | 7/2004 | Freyman |
| 2004/0133156 A1 | 7/2004 | Diaz et al. |

(56) References Cited

U.S. PATENT DOCUMENTS

| | | |
|---|---|---|
| 2004/0147871 A1 | 7/2004 | Burnett |
| 2004/0153049 A1 | 8/2004 | Hewitt et al. |
| 2004/0153051 A1 | 8/2004 | Israelsson et al. |
| 2004/0158231 A1 | 8/2004 | Tanghoj et al. |
| 2004/0163980 A1 | 8/2004 | Tanghoj et al. |
| 2004/0176747 A1 | 9/2004 | Feneley |
| 2004/0249343 A1 | 12/2004 | Cioanta |
| 2004/0254562 A1 | 12/2004 | Tanghoj et al. |
| 2004/0256264 A1 | 12/2004 | Israelsson et al. |
| 2005/0015076 A1 | 1/2005 | Giebmeyer et al. |
| 2005/0031872 A1 | 2/2005 | Schmidt et al. |
| 2005/0033222 A1 | 2/2005 | Haggstrom et al. |
| 2005/0043715 A1 | 2/2005 | Nestenborg et al. |
| 2005/0049577 A1 | 3/2005 | Snell et al. |
| 2005/0059990 A1 | 3/2005 | Ayala et al. |
| 2005/0065499 A1 | 3/2005 | Douk et al. |
| 2005/0070882 A1 | 3/2005 | McBride |
| 2005/0080399 A1 | 4/2005 | Bolmsjo et al. |
| 2005/0096582 A1 | 5/2005 | Burnett |
| 2005/0101923 A1 | 5/2005 | Elson et al. |
| 2005/0101924 A1 | 5/2005 | Elson et al. |
| 2005/0107735 A1 | 5/2005 | Lennox et al. |
| 2005/0109648 A1 | 5/2005 | Kerzman et al. |
| 2005/0137522 A1 | 6/2005 | Aoki |
| 2005/0137582 A1 | 6/2005 | Kull-Osterlin et al. |
| 2005/0143690 A1 | 6/2005 | High |
| 2005/0148950 A1 | 7/2005 | Windheuser et al. |
| 2005/0197531 A1 | 9/2005 | Cabiri et al. |
| 2005/0199521 A1 | 9/2005 | Givens |
| 2005/0209580 A1 | 9/2005 | Freyman |
| 2005/0214443 A1 | 9/2005 | Madsen |
| 2005/0245901 A1 | 11/2005 | Floyd |
| 2005/0251108 A1 | 11/2005 | Frassica |
| 2005/0256447 A1 | 11/2005 | Richardson et al. |
| 2005/0273034 A1 | 12/2005 | Burnett |
| 2005/0283136 A1 | 12/2005 | Skarda |
| 2006/0025753 A1 | 2/2006 | Kubalak et al. |
| 2006/0030864 A1 | 2/2006 | Kennedy, et al. |
| 2006/0036208 A1 | 2/2006 | Burnett |
| 2006/0041246 A1 | 2/2006 | Provost-tine et al. |
| 2006/0058777 A1 | 3/2006 | Nielsen |
| 2006/0064065 A1 | 3/2006 | Russo |
| 2006/0079835 A1 | 4/2006 | Frassica |
| 2006/0079854 A1 | 4/2006 | Kay et al. |
| 2006/0122566 A1 | 6/2006 | Huang et al. |
| 2006/0122568 A1 | 6/2006 | Elson et al. |
| 2006/0163097 A1 | 7/2006 | Murray et al. |
| 2006/0184112 A1 | 8/2006 | Horn et al. |
| 2006/0184145 A1 | 8/2006 | Ciok et al. |
| 2006/0196783 A1 | 9/2006 | Bruun et al. |
| 2006/0263404 A1 | 11/2006 | Nielsen et al. |
| 2006/0271019 A1 | 11/2006 | Stoller et al. |
| 2006/0276894 A1 | 12/2006 | Finley |
| 2006/0278546 A1* | 12/2006 | State et al. ............... 206/364 |
| 2006/0278547 A1* | 12/2006 | Rowe et al. ............... 206/364 |
| 2006/0293642 A1 | 12/2006 | Israelsson et al. |
| 2007/0005041 A1 | 1/2007 | Frassica et al. |
| 2007/0010798 A1 | 1/2007 | Stoller et al. |
| 2007/0016169 A1 | 1/2007 | Utas et al. |
| 2007/0049879 A1 | 3/2007 | Gutierrez |
| 2007/0066963 A1 | 3/2007 | Tanghoj |
| 2007/0106233 A1 | 5/2007 | Huang et al. |
| 2007/0112327 A1 | 5/2007 | Yun et al. |
| 2007/0149929 A1 | 6/2007 | Utas et al. |
| 2007/0197957 A1 | 8/2007 | Hunter et al. |
| 2007/0225635 A1 | 9/2007 | Lynn |
| 2007/0225687 A1 | 9/2007 | House |
| 2007/0244449 A1 | 10/2007 | Najafi et al. |
| 2008/0006554 A1 | 1/2008 | Duffy et al. |
| 2008/0015518 A1 | 1/2008 | Huang et al. |
| 2008/0021382 A1 | 1/2008 | Freyman |
| 2008/0027414 A1 | 1/2008 | Tanghoj et al. |
| 2008/0033471 A1 | 2/2008 | Paz et al. |
| 2008/0050446 A1 | 2/2008 | Ziegler et al. |
| 2008/0051762 A1 | 2/2008 | Tsukada et al. |
| 2008/0051763 A1 | 2/2008 | Frojd |
| 2008/0077099 A1 | 3/2008 | House |
| 2008/0082051 A1 | 4/2008 | Miller et al. |
| 2008/0085949 A1 | 4/2008 | McGhee |
| 2008/0091145 A1 | 4/2008 | House |
| 2008/0097362 A1 | 4/2008 | Mosler et al. |
| 2008/0097394 A1 | 4/2008 | Lampropoulos et al. |
| 2008/0097411 A1 | 4/2008 | House |
| 2008/0140010 A1 | 6/2008 | Kennedy et al. |
| 2008/0140052 A1 | 6/2008 | Moller et al. |
| 2008/0171973 A1 | 7/2008 | House |
| 2008/0171998 A1 | 7/2008 | House |
| 2008/0172016 A1 | 7/2008 | House |
| 2008/0172042 A1 | 7/2008 | House |
| 2008/0179208 A1 | 7/2008 | Murray et al. |
| 2008/0200907 A1 | 8/2008 | Nestenborg |
| 2008/0243091 A1 | 10/2008 | Humphreys et al. |
| 2008/0249467 A1 | 10/2008 | Burnett et al. |
| 2008/0249482 A1 | 10/2008 | Erez |
| 2008/0275463 A1 | 11/2008 | High |
| 2009/0024111 A1 | 1/2009 | Borodulin et al. |
| 2009/0048537 A1 | 2/2009 | Lydon et al. |
| 2009/0054876 A1 | 2/2009 | Borodulin et al. |
| 2009/0065605 A1 | 3/2009 | Roche et al. |
| 2009/0071851 A1* | 3/2009 | Maki et al. ............... 206/210 |
| 2009/0131917 A1 | 5/2009 | Kavanagh et al. |
| 2009/0137985 A1 | 5/2009 | Tanghoej et al. |
| 2009/0137986 A1 | 5/2009 | Golden et al. |
| 2009/0149837 A1 | 6/2009 | Tanghoj et al. |
| 2009/0156882 A1 | 6/2009 | Chi Sing et al. |
| 2009/0200187 A1 | 8/2009 | Nestenborg et al. |
| 2009/0299334 A1 | 12/2009 | Nishtala et al. |
| 2010/0263327 A1 | 10/2010 | Murray et al. |
| 2010/0324540 A1 | 12/2010 | Paulen et al. |
| 2011/0028943 A1* | 2/2011 | Lawson et al. ............. 604/544 |
| 2011/0056852 A1 | 3/2011 | Frojd |
| 2011/0114520 A1 | 5/2011 | Matthison-Hansen |
| 2011/0127186 A1* | 6/2011 | Enns et al. ............... 206/364 |
| 2011/0137296 A1 | 6/2011 | Tanghoj |
| 2011/0184386 A1 | 7/2011 | House |
| 2012/0168324 A1 | 7/2012 | Carleo |
| 2012/0179102 A1 | 7/2012 | Blanchard et al. |
| 2012/0316515 A1 | 12/2012 | Terry |
| 2013/0006226 A1* | 1/2013 | Hong et al. ............... 604/544 |
| 2013/0048516 A1 | 2/2013 | Nishtala et al. |
| 2013/0153446 A1 | 6/2013 | Utas et al. |
| 2013/0186778 A1 | 7/2013 | Terry |

FOREIGN PATENT DOCUMENTS

| | | |
|---|---|---|
| EP | 0217771 | 4/1987 |
| EP | 247559 A1 | 12/1987 |
| EP | 0252918 A1 | 1/1988 |
| EP | 0479935 A1 | 4/1992 |
| EP | 0677299 | 10/1995 |
| EP | 0699086 A1 | 3/1996 |
| EP | 0815037 A1 | 1/1998 |
| EP | 0909249 A1 | 4/1999 |
| EP | 0923398 | 6/1999 |
| EP | 0935478 A1 | 8/1999 |
| EP | 0959930 | 12/1999 |
| EP | 0977610 A2 | 2/2000 |
| EP | 1023882 | 8/2000 |
| EP | 1090656 | 4/2001 |
| EP | 1115450 A1 | 7/2001 |
| EP | 1131022 A1 | 9/2001 |
| EP | 1145729 | 10/2001 |
| EP | 1175355 A1 | 1/2002 |
| EP | 1237615 A1 | 9/2002 |
| EP | 1245205 | 10/2002 |
| EP | 1308146 | 5/2003 |
| EP | 1406690 A2 | 4/2004 |
| EP | 1409060 A2 | 4/2004 |
| EP | 1420846 A1 | 5/2004 |
| EP | 1420847 A2 | 5/2004 |
| EP | 1427467 A2 | 6/2004 |
| EP | 1498151 | 1/2005 |
| EP | 1629860 | 3/2006 |
| EP | 1641510 A1 | 4/2006 |

(56) References Cited

FOREIGN PATENT DOCUMENTS

| | | |
|---|---|---|
| EP | 1642610 | 4/2006 |
| EP | 1642611 | 4/2006 |
| EP | 2060296 A1 | 5/2009 |
| EP | 2459264 A1 | 6/2012 |
| EP | 2464411 A1 | 6/2012 |
| EP | 2515988 A1 | 10/2012 |
| EP | 2542291 A1 | 1/2013 |
| FR | 2731345 A1 | 9/1996 |
| GB | 2284764 | 6/1995 |
| GB | 2319507 | 5/1998 |
| JP | 2013-500125 | 1/2013 |
| JP | 2013-515572 | 5/2013 |
| WO | 8401296 A1 | 4/1984 |
| WO | 8606284 | 11/1986 |
| WO | 9105577 A1 | 5/1991 |
| WO | 9416747 A1 | 8/1994 |
| WO | 9638192 A1 | 12/1996 |
| WO | 9726937 | 7/1997 |
| WO | 9741811 | 11/1997 |
| WO | 9806642 | 2/1998 |
| WO | 9811932 | 3/1998 |
| WO | 9819729 | 5/1998 |
| WO | 9930761 A1 | 6/1999 |
| WO | 0016843 | 3/2000 |
| WO | 0047494 | 8/2000 |
| WO | 0143807 | 6/2001 |
| WO | 0152763 | 7/2001 |
| WO | 0193935 | 12/2001 |
| WO | 0236192 | 5/2002 |
| WO | 03002177 | 1/2003 |
| WO | 03002178 | 1/2003 |
| WO | 03008028 | 1/2003 |
| WO | 03008029 | 1/2003 |
| WO | 03064279 A1 | 8/2003 |
| WO | 03092779 | 11/2003 |
| WO | 2004030722 | 4/2004 |
| WO | 2004045696 | 6/2004 |
| WO | 2004045696 A1 | 6/2004 |
| WO | 2004050155 | 6/2004 |
| WO | 2004052440 | 6/2004 |
| WO | 2004056414 | 7/2004 |
| WO | 2004075944 | 9/2004 |
| WO | 2004089454 | 10/2004 |
| WO | 2005004964 | 1/2005 |
| WO | 2005014055 A2 | 2/2005 |
| WO | 2005061035 | 7/2005 |
| WO | 2005092418 | 10/2005 |
| WO | 2007050685 | 5/2007 |
| WO | 2007050685 A2 | 5/2007 |
| WO | 2009012336 A1 | 1/2009 |
| WO | 2007050685 A3 | 4/2009 |
| WO | 2011014201 A1 | 2/2011 |
| WO | 2011019359 A1 | 2/2011 |
| WO | 2011063816 A1 | 6/2011 |
| WO | 2011079129 A1 | 6/2011 |
| WO | 2011109393 A1 | 9/2011 |
| WO | 2014165046 A1 | 10/2014 |

OTHER PUBLICATIONS

CN 201080058895.4 filed Jun. 21, 2012 First Office Action dated Feb. 27, 2014.
EP 09848341.5 filed Feb. 27, 2012 extended European Search Report dated Apr. 4, 2013.
EP 09848341.5 filed Feb. 27, 2012 supplemental European Search Report dated Nov. 8, 2013.
EP 10840071.4 filed Jul. 4, 2012 Exam Report dated Apr. 29, 2014.
EP 10840071.4 filed Jul. 4, 2012 extended European Search Report dated Apr. 17, 2013.
EP 11751198.0 filed Sep. 28, 2012 Exam Report dated Feb. 7, 2014.
EP 11751198.0 filed Sep. 28, 2012 extended European search report dated Jul. 9, 2013.
PCT/US2006/041633 filed Oct. 25, 2006 International Preliminary Report on Patentability dated Mar. 24, 2009.
PCT/US2006/041633 filed Oct. 25, 2006 Search Report dated Aug. 12, 2008.
PCT/US2006/041633 filed Oct. 25, 2006 Written Opinion dated Aug. 12, 2008.
PCT/US2009/055389 filed Aug. 28, 2009 International Search Report dated Oct. 20, 2009.
PCT/US2009/055389 filed Aug. 28, 2009 Written Opinion dated Oct. 20, 2009.
PCT/US2009/055395 filed Aug. 28, 2009 International Preliminary Report on Patentability dated Jan. 31, 2012.
PCT/US2009/055395 filed Aug. 28, 2009 International Search Report dated Oct. 15, 2009.
PCT/US2009/055395 filed Aug. 28, 2009 Written Opinion dated Oct. 15, 2009.
PCT/US2010/061597 filed Dec. 21, 2010 International Preliminary Report on Patentability dated Jun. 26, 2012 and Written Opinion dated Feb. 28, 2011.
PCT/US2010/061597 filed Dec. 21, 2010 International Search Report dated Feb. 28, 2011.
PCT/US2011/026681 filed Mar. 1, 2011 International Preliminary Report on Patentability dated Sep. 4, 2012.
PCT/US2011/026681 filed Mar. 1, 2011 International Search Report dated Apr. 27, 2011.
PCT/US2011/026681 filed Mar. 1, 2011 Written Opinion dated Apr. 27, 2011.
U.S. Appl. No. 12/091,916, filed Feb. 2, 2009 Final Office Action dated Sep. 22, 2011.
U.S. Appl. No. 12/091,916, filed Feb. 2, 2009 Non-Final Office Action dated May 10, 2011.
U.S. Appl. No. 12/091,916, filed Feb. 2, 2009 Non-Final Office Action dated Nov. 24, 2010.
U.S. Appl. No. 12/091,916, filed Feb. 2, 2009 Notice of Allowance dated Aug. 17, 2012.
U.S. Appl. No. 13/387,447, filed Mar. 22, 2012 Advisory Action dated Feb. 27, 2014.
U.S. Appl. No. 13/387,447, filed Mar. 22, 2012 Final Office Action dated Dec. 11, 2013.
U.S. Appl. No. 13/387,447, filed Mar. 22, 2012 Non-Final Office Action dated Jan. 15, 2013.
U.S. Appl. No. 13/387,447, filed Mar. 22, 2012 Non-Final Office Action dated Jul. 15, 2014.
U.S. Appl. No. 13/387,447, filed Mar. 22, 2012 Non-Final Office Action dated Jun. 6, 2013.
U.S. Appl. No. 13/389,753, filed Mar. 20, 2012 Non-Final Office Action dated Jul. 21, 2014.
JP 2012-546157 filed Jun. 12, 2012 First Office Action dated Sep. 16, 2014.
PCT/US2014/024231 filed Mar. 12, 2014 International Search Report and Written Opinion dated Jul. 10, 2014.
U.S. Appl. No. 13/582,698, filed Sep. 4, 2012 Non-Final Office Action dated Sep. 24, 2014.
U.S. Appl. No. 13/662,278, filed Oct. 26, 2012 Non-Final Office Action dated Sep. 12, 2014.

\* cited by examiner

ENHANCED PRE-WETTED INTERMITTENT CATHETER WITH LUBRICIOUS COATING

Intermittent catheters are generally catheters or tubes having a rounded tip connected to a distal end that is inserted into the bladder of a patient or user, and a molded funnel connected to a proximal end that remains outside the body of the patient or user. These types of catheters are typically utilized on a temporary basis to remove urine from the bladder of a patient or user. The distal tip may include slots or openings on the shaft to facilitate drainage of urine therefrom once the tip is positioned inside the bladder. Pre-wetted intermittent catheters are intermittent catheters having a highly lubricious coating on an outer surface thereof, which are packaged or otherwise brought into contact with fluid in order to provide a catheter with a slippery outer surface to facilitate insertion into the patient or user.

Intermittent catheters are well-known in the art, and include those disclosed in U.S. Pat. Nos. 5,895,374; 6,059,107; 6,634,498; 7,311,698; 6,849,070, 7,615,045; 6,736,805; 7,087,048; 7,380,658; and 6,355,004, the disclosures of which are all incorporated herein by reference in their entirety as if fully set forth herein.

The current offerings of pre-wetted intermittent catheters can be broken up into three broad categories. In the first type, the catheter is packaged in a dry environment, but contains a lubricious coating that requires a wetting fluid in order to become hydrated. The wetting fluid is obtained from an external source by the user (e.g., sink, bottled water, etc.) and the catheter is positioned within the wetting fluid for a period of time to become hydrated. Use of this first type of intermittent catheter may prove difficult in the event that drainage must be performed by the user when no clean water or wetting fluid is available. Moreover, sterility of the catheter may be compromised due to the handling of the catheter by the user as wetting fluid is applied and thereafter during insertion.

A second type of pre-wetted intermittent catheter is also packaged in a dry environment and contains a lubricious coating. In this second type, the wetting fluid is positioned in a pouch or container within the catheter package itself such that to hydrate the catheter, the pouch or container must be opened when the user is ready for insertion. A third type of pre-wetted intermittent catheter is packaged in a wet environment (i.e., the catheter is exposed to a wetting fluid within the catheter package).

Intermittent catheterization is generally performed a minimum of three times a day by the patient or a care giver in order to drain the bladder. The genital area near the urethral opening is wiped with an antiseptic agent, such as iodine. A lubricant may then be used to facilitate the entry of the catheter into the urethra. A topical local anesthetic may also be applied to numb the urethral opening during the procedure. The catheter packaging is opened, and the catheter is removed. One end of the catheter is placed in a container, and the other end is inserted into and guided up the urethra and into the bladder until urine flow begins.

Some patients requiring intermittent catheterization may have limited dexterity resulting from, for example, traumatic brain or spinal cord injury, or a disease state (e.g., spina bifida, multiple sclerosis). Such patients may have difficulty opening the packaging of an intermittent catheter, and may further have difficulty during insertion. Fumbling with the catheter and/or its packaging is potentially harmful to the patient, because the sterile surfaces of the catheter may become non-sterile. Inserting a non-sterile urinary catheter increases the likelihood of contracting a urinary tract infection.

Packaging is a separate issue associated with intermittent urinary catheterization. It could be desirable to provide an intermittent urinary catheter in a discrete, compact packaged unit to improve the ease of use, convenience, and privacy of the intermittent catheterization process for the user.

Thus, there is a need for an intermittent catheter that addresses at least one of the needs of the patient or user, e.g., is easy to use, is quick, clean, compact, capable of use with or without a bag, and is capable of maintaining sterility during insertion procedures.

BRIEF SUMMARY OF THE INVENTION

Accordingly, a packaged urinary catheter is described herein, comprising a conduit having a proximal end and a distal end, wherein the distal end comprises at least one aperture for receiving urine from the bladder; a sleeve having a length, a width, and a size configured to receive the conduit, wherein the sleeve surrounds substantially the entire length of the conduit; and wherein the conduit and the sleeve are arranged in a helical coil.

In one embodiment, the shape of the helical coil is maintained by portions of the sleeve being releasably fixed together along at least a portion of the length of the sleeve.

In another embodiment, a first cap seals a proximal end of the sleeve, and a second cap seals a distal end of the sleeve.

In another embodiment, at least one of the first and second caps comprises a gripping feature configured to be grasped by a patient or user of the packaged urinary catheter.

In another embodiment, the gripping feature is sized and shaped to receive a finger therethrough.

In another embodiment, portions of the sleeve are releasably fixed together by a perforated section along a length of the sleeve.

In another embodiment, the packaged urinary catheter is released from the helical coil configuration by grasping the first and second caps, and urging the caps in substantially different directions.

In one embodiment, a lubricating material is contained within the sleeve.

In another embodiment, the lubricating material is chosen from water, a hydrogel, and a vapor.

In another embodiment, at least a portion of the outer surface of the conduit is hydrophilic.

In another embodiment, there is disclosed a synthetic polyisoprene conduit having a proximal end and a distal end, wherein the distal end comprises at least one aperture for receiving urine from the bladder; a sleeve having a length, and a width, and a size configured to receive the conduit, wherein the sleeve surrounds substantially the entire length of the conduit; and wherein the conduit and the sleeve are arranged in a helical coil.

These and other embodiments, methods, features and advantages will become more apparent to those skilled in the art when taken with reference to the following more detailed description of the invention in conjunction with the accompanying drawings that are first briefly described.

DESCRIPTION OF THE INVENTION

Figure 1:
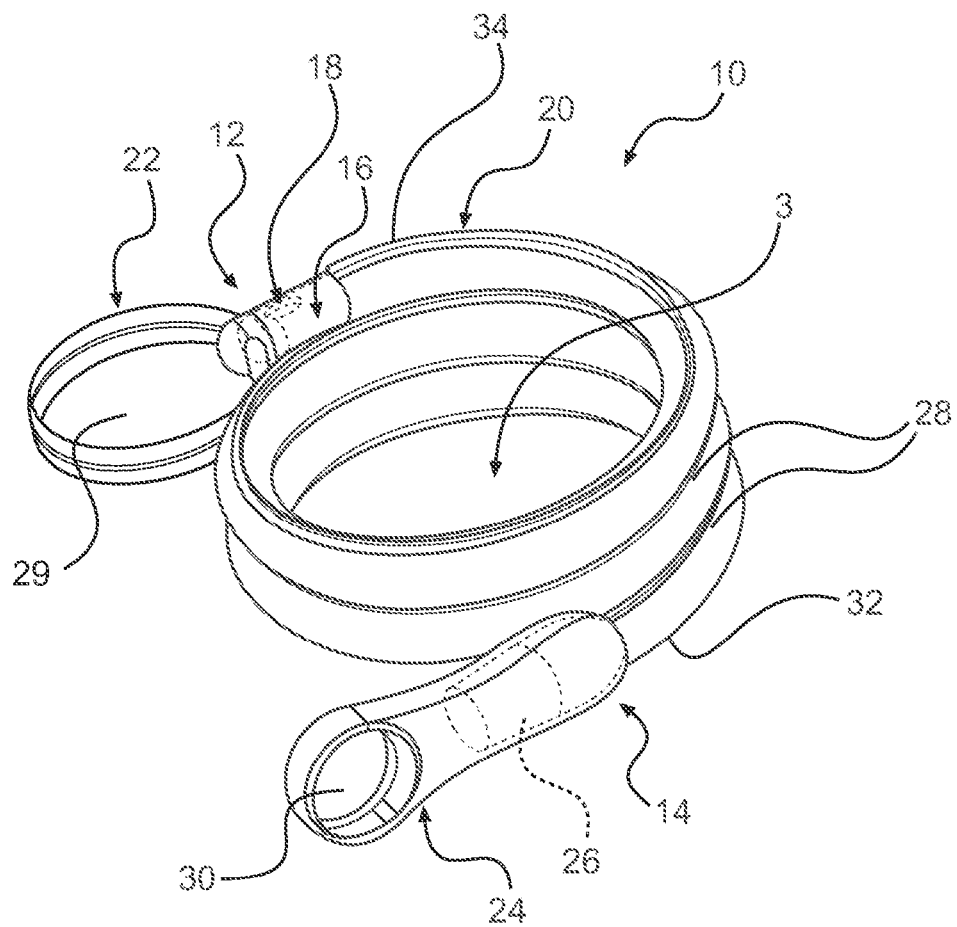
FIG. 1 illustrates one embodiment of an intermittent catheter according to the present disclosure.

The following description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the reference terms "proximal" and "distal" (proximal being closer than distal) refer to the proximity with respect to a health care professional or other person other than a patient that is assisting the patient in using the catheter apparatus. In the case that a user is implementing the catheter apparatus without the aid of another, "proximal" and "distal" refer to the proximity with respect to a point external to the user's body. Thus, for example, a region or section of the catheter apparatus that is close to a health care professional or the user's hand when the catheter apparatus is being utilized is referred to as "proximal," while a region or section of the catheter apparatus distanced from a health care professional or the user's hand when the catheter apparatus being used is referred to as "distal."

The packaged catheter, as described herein, is discussed in the context of a urinary catheter for insertion into a user/patient bladder for drainage of urine therefrom. However, it should be appreciated that the packaged catheter described could also be used for other applications not specifically mentioned herein, and therefore should not be limited to a urinary catheter application.

Generally, the packaged catheter includes a conduit, such as a catheter or tube, positioned within a sleeve. The conduit may have a round cross-sectional shape, an oval cross-sectional shape, or any other cross-sectional shape that may facilitate insertion into a user's body, and in particular into a user's bladder through the urethra. The conduit, in accordance with various embodiments, contains a lubricious and/or antimicrobial coating on at least an outer surface thereof. The lubricious coating can include a hydrogel or any coating that renders the surface of the conduit hydrophilic. Suitable non-limiting examples of such coatings that may be used on the catheters disclosed herein may be found in U.S. Pat. Nos. 6,329,488; 6,716,895; and 6,949,598; U.S. Patent Application Publication No. US 2004/0116551; and U.S. patent application Ser. No. 13/383,535, filed Jan. 11, 2012, which is a National Phase application of International Application No. PCT/US2011/62086, titled "Deposition of a Silver Layer on a Non-Conducting Substrate," and published as WO 2012/071536. Each of the above-listed patents, publications, and applications is incorporated by reference into this application as if fully set forth herein.

Figure 2:
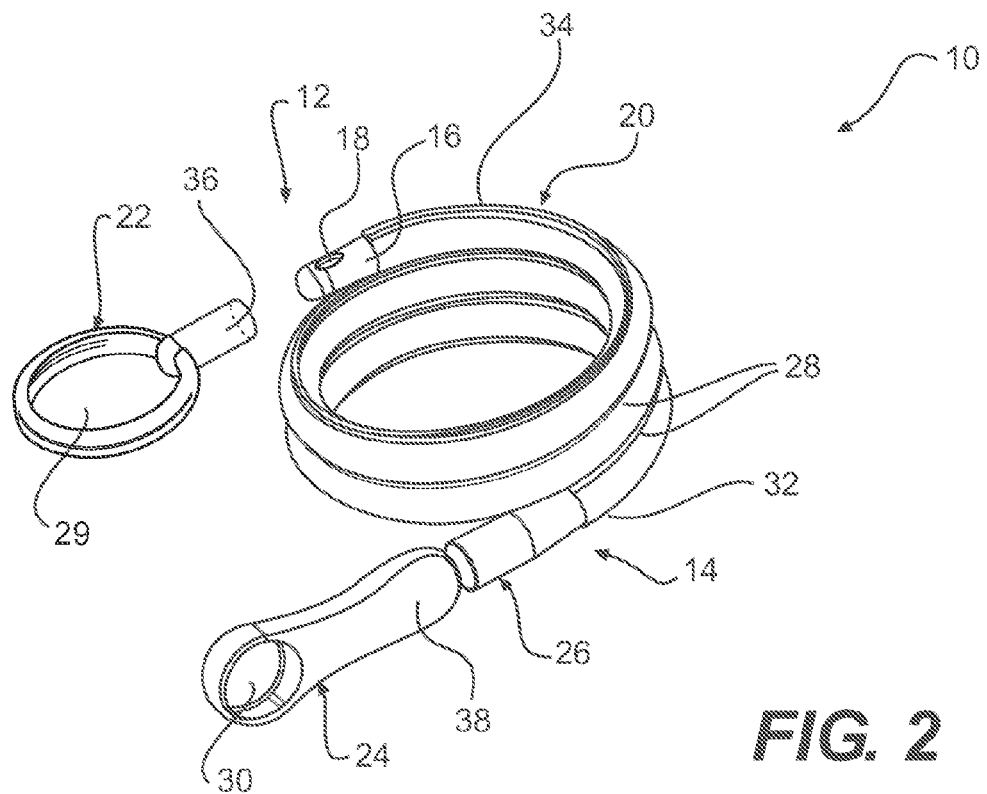
FIG. 2 illustrates one embodiment of an intermittent catheter in accordance with the present disclosure, with the end caps removed.

Referring now to FIGS. 1-2, one embodiment of a packaged urinary catheter 10 is shown, including a conduit 16 disposed within a flexible sleeve 20. Conduit 16 has a proximal end 14, a distal end 12, an eyelet 18 to receive urine, and a funnel 26 to dispense urine. The connection between the conduit 16 and the funnel 26 can be accomplished by any method known to bond such materials together, for example by molding and or chemically bonding (with, e.g., cyclohexanone). Sleeve 20 has a length, a width, and a size configured to receive the conduit 16, and the sleeve surrounds substantially the entire length of the conduit 16.

According to certain embodiments, the sleeve 20 is made of a gas impermeable material, such as a polymer, for example polypropylene or polyethylene. According to one embodiment, sleeve 20 is made of a non-rigid material, such as, for example, a foil material or the like, or films, such as polymeric films, for example polypropylene and polyethylene films. The sleeve may be constructed from two blanks of material that are joined at the edges to form the sleeve. The edges of the blanks may be joined by typical methods known to those of ordinary skill in the art, including heat, sonic, chemical, or physical bonding.

According to one embodiment, the sleeve 20 is configured to collapse upon itself to facilitate introduction of the conduit by a user and to prevent direct contact by the user with the conduit. The sleeve 20 may include an introduction member (not shown) at the proximal end thereof to facilitate introduction of the conduit to facilitate disposal of the drained urine. A suitable non-limiting example of an introducer is disclosed in U.S. Pat. No. 4,692,154 (the disclosure of which is incorporated herein by reference in its entirety).

According to various embodiments, the sleeve contains within it a wetting fluid. The purpose of the wetting fluid is to maintain hydration of a lubricious coating on the conduit 16 such that upon insertion of the conduit into a user, at least an outer portion thereof is extremely slippery, facilitating insertion.

The packaged catheter 10 includes first cap 24 for covering the proximal end 14 of conduit 16, and a second cap 22 for covering distal end 12 of conduit 16. The distal cap 22 has a lumen 36 (FIG. 2) configured to receive the distal tip of conduit 16. According to one embodiment, the lumen 36 receives both the distal tip of the conduit 16 and the distal end of the sleeve 20. According to another embodiment, the distal end of the sleeve is releasably joined to the proximal end of cap 22. According to yet another embodiment, the inside diameter of sleeve 20 is joined to the outside diameter of lumen 36.

Similarly, proximal cap 24 has a lumen 38 configured to receive the funnel 26 of conduit 16. According to one embodiment, the lumen 38 receives both the funnel and the proximal end of the sleeve 20. According to another embodiment, the proximal end of the sleeve 20 is releasably joined to the distal end of cap 24. According to yet another embodiment, the inside diameter of lumen 38 is releasably joined to the outside diameter of 20.

Patients who self-catheterize may have limited dexterity. Accordingly, it could be advantageous to provide caps 22 and 24 with grasping features to facilitate removal by those of limited dexterity. According to certain embodiments, caps 22 and 24 may have apertures 29 and 30, respectively, sized and shaped to receive at least one finger. Other grasping features known to those of ordinary skill in the art are also within the scope of the present disclosure.

According to certain embodiments, the sleeve 20 may have a tubular outer surface with a plurality of pre-formed pleats or folds (not shown) along a middle portion thereof between a proximal end section 32 and a distal end section 34 of packaged catheter 10. The pleats or folds in the outer surface of the sleeve 20 permit the sleeve to compress or collapse upon itself in accordion-like fashion. According to another embodiment, the sleeve 20 does not contain pre-formed pleats or folds, but instead is comprised of a thin, substantially flat, collapsible material.

The packaged catheter according to the present disclosure is designed to provide a compact configuration for discreet transport and usage. This may be accomplished by providing the catheter in a folded or coiled configuration. The present disclosure contemplates helical coils, as well as flat coils, or coils having any other configuration suitable for packaging. Such a configuration may allow a user to stow a sufficient number of catheters in a backpack, purse, or pocket while preserving the user's privacy and dignity.

Figure 3:
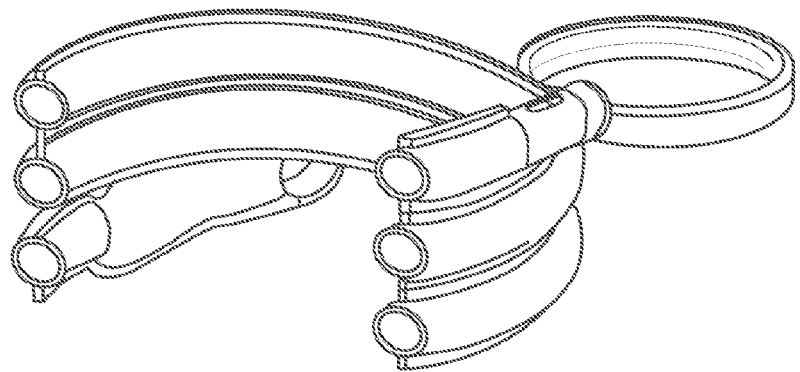
FIG. 3 illustrates a cutaway view of one embodiment of an intermittent catheter in accordance with the present disclosure.
Figure 4:
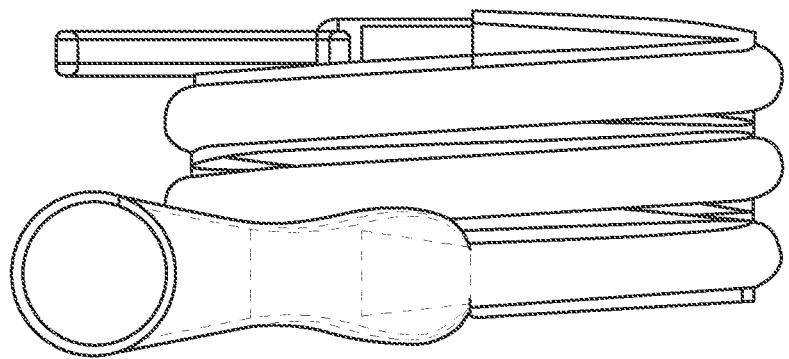
FIG. 4 illustrates a side view of one embodiment of an intermittent catheter in accordance with the present disclosure.

FIGS. 1-2 show a packaged urinary catheter in a coiled configuration. According to one embodiment, the "coils" of the packaged catheter are held together at joined edges 28 of the sleeve 20. The joined edges 28 can be held together by a perforation in the sleeve 20, or by any conventional bonding method known to those of ordinary skill in the art. The packaged catheter 10 is shown in cross-section in FIG. 3. A side view of the packaged catheter 10 is shown in FIG. 4.

Figure 7A:
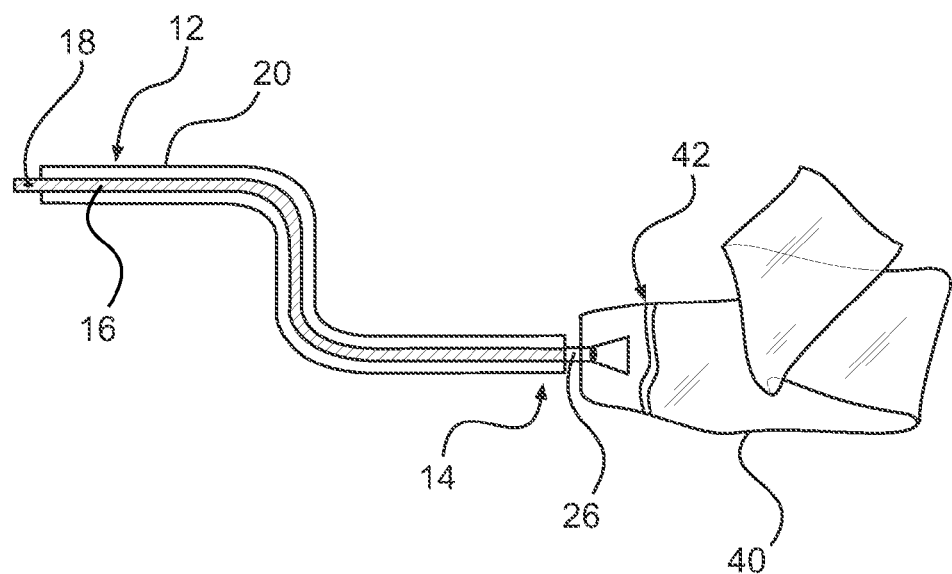
FIG. 7A illustrates the proximal end of an intermittent catheter in a urine disposal bag, in accordance with one aspect of the present disclosure.

Cap 24 is configured for removal from the distal end 14 of the packaged catheter, and urine is permitted to drain from funnel 26. In one embodiment, the drainage funnel 26 of the conduit 16 is configured such that it can be inserted into, or otherwise connected to, a bag 40 (FIG. 7) and sealed (or at least partially sealed) thereto such that fluid communication between the funnel 26 and the bag is established and a closed system is provided to prevent exposure to contaminants to the user or assistant (nurse, family member, etc.). Drainage of a user's bladder can then take place directly into the bag 40, which can subsequently be detached from the funnel 26 and either emptied and sanitized, or disposed of, in the case that the bag is made of a disposable material.

In one embodiment the bag includes an extension member (not shown) extending from an opening therein that both connects to the funnel 26 and is shaped to receive the cap 24. According to another embodiment, the bag has a closure member 42 at the distal end thereof, allowing the bag to be closed once the catheterization process is completed. According to another embodiment, the bag 40 is sized and shaped to hold a volume of urine and the used catheter and sleeve. According to yet another embodiment, the bag 40 is packaged together with the catheter. For example, the bag can be provided in a folded configuration in the center 3 of the coiled catheter (FIG. 1), thus minimizing the total space occupied by the packaged catheter 10.

Figure 7B:
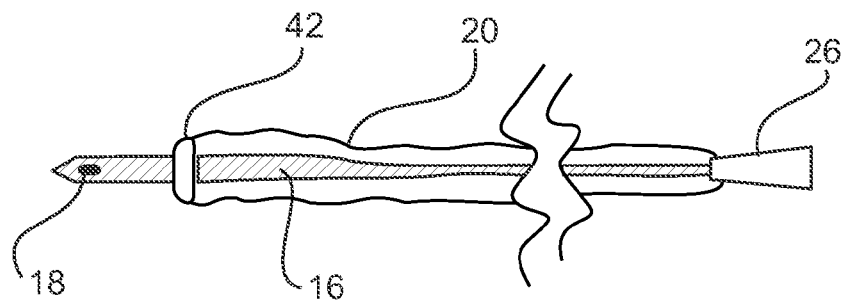
FIG. 7B illustrates a sealing washer at the distal end of a catheter sleeve, in accordance with one aspect of the present disclosure.

According to one embodiment, and as exemplified in FIG. 7B, a sliding seal member 42, such as a compressible washer, is incorporated into the distal end sleeve 20, through which the conduit 16 is slidably positioned, to permit sliding of the conduit 16 with respect to the sleeve 20. The seal formed between sleeve 20 and sliding seal member 42, and between sliding seal member 42 and conduit 16, may serve a number of purposes. For example, the seals may help to minimize exposure of the outer surface of the conduit 16 to the environment, thus minimizing an infection risk. In addition, the seals may prevent loss or leakage of the wetting fluid from the volume formed between the inside surface of sleeve 20 and the outside surface of conduit 16. The inside diameter of the end of sleeve 20 may be bonded to the outside diameter of the seal member 42.

The catheter may have a round or substantially round cross-sectional shape, an oval cross-sectional shape, or any other cross-sectional shape that may facilitate insertion into the body of a user/patient, and in particular, into the bladder of the user/patient through the urethra. According to various embodiments, the shape of the catheter can also be variable along its length.

Different lengths, sizes (e.g., diameter, width, etc.), and configurations are possible for the conduit 16, depending on the user's anatomy. For female users, the insertable length may range from 40 to 100 mm, for example 50 to 80 mm, such as 55 to 75 mm. For male users, the insertable length can range from 100 to 300 mm, such as 190 to 240 mm, for example 230 mm. For example, in one embodiment for an adult male human, the length of the conduit 16 may be in the range of about 8 to about 18 cm and have an elliptical cross-sectional shape similar to the shape of the male urethra.

The proximal end of the conduit 16 includes a tip having a rounded atraumatic shape (e.g., bullet shape, etc.) and at least one opening 18 or "eyes" in the sides of the tip that connect with a central conduit lumen such that placement of the conduit tip into a urine pool in the bladder results in drainage of urine therefrom. The tip design can vary according to the needs of a user, for example, the catheters disclosed herein can be provided with a coude tip.

As mentioned above, at least a portion of the outer surface of the conduit 16 is coated with a lubricious coating, which when contacted by a wetting fluid, becomes hydrated. The hydration of the lubricious coating results in a surface with a low coefficient of friction such that the conduit 16 is easily slidable into the body of a user. The lubricious coating is made from a material such as those described in U.S. Pat. No. 6,329,488 or 4,642,267, the disclosures of which are incorporated herein by reference in their entirety.

Figure 5:
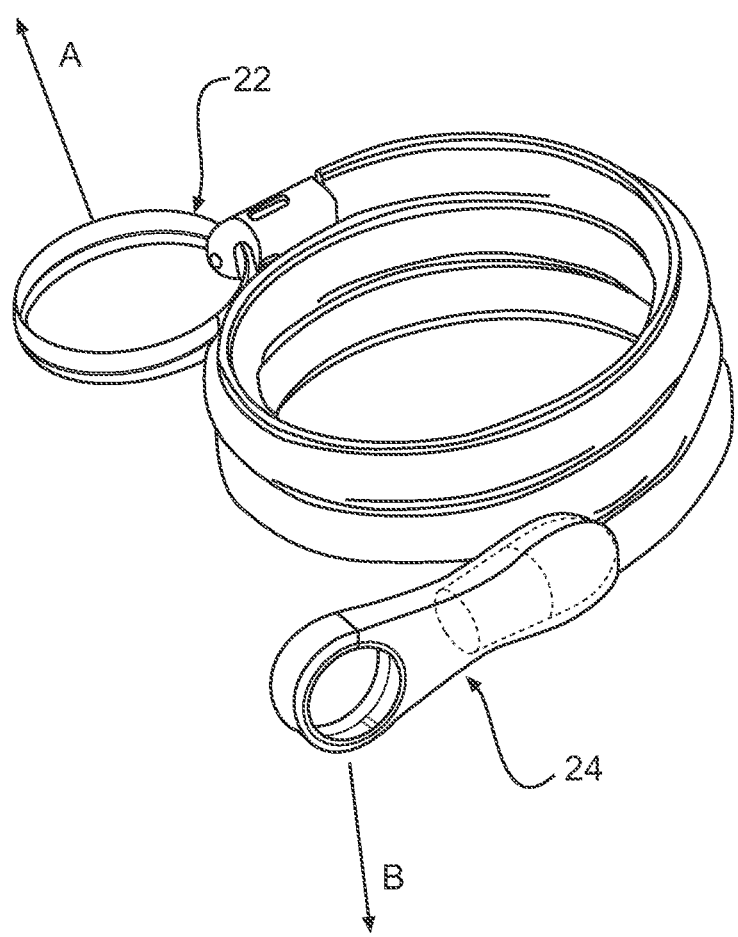
FIG. 5 illustrates one embodiment of an intermittent catheter in accordance with the present disclosure.
Figure 6:
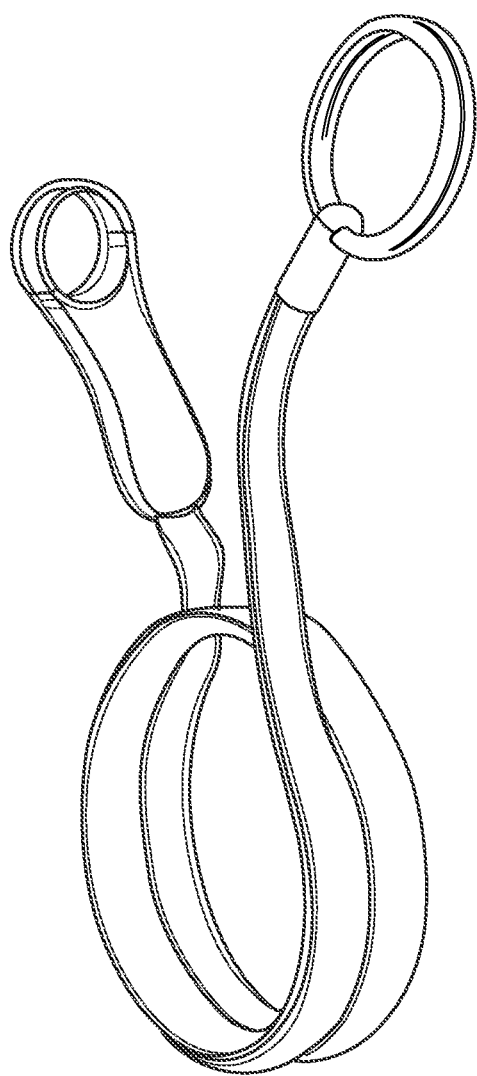
FIG. 6 illustrates an intermittent catheter in a partially deployed configuration, in accordance with one aspect of the present disclosure.

One of the advantages associated with the packaged catheter of the present disclosure is ease of use. From the coiled configuration, a user can grab each of caps 22 and 24, optionally through apertures 29 and 30, and urge the caps in substantially opposing directions shown by arrows A and B (FIG. 5). The resulting force will uncoil the packaged catheter by allowing the edges 28 of the sleeve 20 to separate (FIG. 6). Once the coils are sufficiently separated, the user can begin the catheterization process. Cap 22 can be secured to the distal end of the conduit 16 or sleeve 20 by friction fit, threaded engagement (i.e., either the cap or the distal end section contains threads, protrusions, etc. while the other contains grooves, detents, recesses, etc. to receive the threads, protrusions, etc.), or other like securing methods known to one skilled in the art. Once cap 22 is removed, the distal end of conduit 16 is inserted into the urethral meatus. According to one embodiment, the conduit is inserted in a way that avoids the user directly touching the surface of the conduit (in order to minimize dragging harmful bacteria into the user's urinary tract). This can be done by manipulating the conduit 16 only through sleeve 20.

Referring now to the device as illustrated in FIGS. 1-7, the packaged catheter 10 as shown in FIG. 1 is coiled. The conduit 16, being contained completely within the sleeve 20 and surrounded by wetting fluid, is in a sterile condition and remains that way due to caps 22 and 24. Cap 24 is removed, and the bag 40, which may be separately packaged or packaged along with the catheter apparatus 10, is connected to the funnel 26 extending from the distal end of the catheter apparatus 10 as shown in FIG. 7A (in alternate embodiments not employing a bag, this step is not performed). According to another embodiment, the packaged catheter has a bag 40 that surrounds cap 24, such that cap 24 is disconnected by manipulating the cap through the bag.

Once the bag 40 has been connected to the catheter apparatus 10 and the user is ready for insertion, the cap 22 is removed from the distal end 12 of the conduit 16, and the conduit tip is placed into the user. The user or assistant then holds the catheter apparatus 10 at a distal end (e.g., the user grasps the funnel 26 with one hand, and the sleeve 20 or washer 42 with the other hand) and pushes in a distal direction to extend the conduit 16 into the user and eventually into the user's bladder, while simultaneously collapsing the sleeve 20 onto itself. This action minimizes or eliminates exposure of the conduit 16 to conditions or contaminants outside of the container. Drainage of urine from the user's bladder then takes place and following evacuation, the proximal end of the catheter apparatus 10 is pulled in a proximal direction, while the distal end of the sleeve 20 (or the sealing member 42) is held in place. This action results in the conduit 16 returning fully inside the sleeve 20 so that the user or assistant is not exposed to potential contaminants. In the embodiment in which a bag 40 is attached to the proximal end 14 (or the funnel 26) of the catheter apparatus 10, the bag 40 is subsequently removed and disposed of (or emptied and sanitized). In an embodiment in which a bag 40 is not attached to the proximal end 14 or funnel 26 of the catheter apparatus 10, the funnel is directed into a disposal collection member or waste disposal apparatus, such as a toilet, during evacuation of the bladder.

The conduit 16 may be constructed from a suitable polymeric material, such as polyvinyl chloride (PVC), silicone, latex or other synthetic rubber. The components of the catheter disclosed herein can also be made from various well-known materials. For example, the portions of the assembly other than the conduit 16 can be made of polyvinyl propylene, polyvinyl chloride, polyethylene, polypropylene, and other types of suitable polymeric materials. The components can be molded or extruded according to well-known manufacturing techniques.

Materials commonly used to make the conduit 16 include, but are not limited to natural rubber latexes (available, for example, from Guthrie, Inc., Tucson, Ariz.; Firestone, Inc., Akron, Ohio; and Centrotrade USA, Virginia Beach, Va.), silicones (available, for example, from GE Silicones, Waterford, N.Y., Wacker Silicones, Adrian, Mich.; and Dow Corning, Inc., Midland, Mich.), polyvinyl chlorides (available, for example, from Kaneka Corp., Inc., New York, N.Y.), polyurethanes (available, for example, from Bayer, Inc., Toronto, Ontario, Rohm & Haas Company, Philadelphia, Pa.; and Ortec, Inc., Greenville, S.C.), plastisols (available, for example, from G S Industries, Bassett, Va.), polyvinyl acetate, (available, for example from Acetex Corp., Vancouver, British Columbia) polyacrylates (available, for example, from Rohm and Haas, Philadelphia, Pa.) and methacrylate copolymers (available, for example, from Heveatex, Inc., Fall River, Mass.). Synthetic and natural rubber latexes, polyurethanes, and silicones are preferred materials. Any combination of the foregoing materials may also be used in making catheters such as are used to produce latex Foley catheters.

The urinary catheter of the present disclosure can be manufactured by a variety of well-known methods. The tubing can be extruded and the funnel injection molded and then cut to the desired length. The tip of the tube can then be closed and rounded by thermoforming (for example, for PVC tubes) or molded (for example, for silicone tubes). Eye holes can then be punched or otherwise formed near the tip of the distal end of the tube to provide an outlet for urine drainage thru the tube when it is inserted into a bladder.

Alternatively, the entire catheter can be fabricated by dip molding. In this procedure, an elongated rod or "form" is dipped into a liquid coating material such as synthetic or natural rubber latex, for example, to form a layer of material on the form. The deposition of material can be increased by first dipping the form into a coagulant solution to coat the form with a film of chemical that causes the latex to coagulate onto the form. Calcium nitrate is commonly used as the coagulant, and other additives may be used to enhance the removal of the tube from the form once the catheter is formed and dried. The form has the shape and dimensions of the lumen of the catheter. The catheter may be formed from a single dip coating of the form or by multiple coating layers. When a suitable material thickness is achieved on a form, the forms are dried to produce the catheter. If multiple coatings are used to form the catheter, each coating may be dried before the next is applied. Once dried, the catheter may be stripped from the form. The catheters may then be washed and dried, and eyelets may then be formed thereon. Further manufacturing steps may be found in U.S. Patent Application Publication No. US 2004/0133156, the disclosure of which is incorporated by reference herein.

This invention has been described and specific examples of the invention have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. A packaged urinary catheter, comprising:
    a conduit having a proximal end and a distal end, wherein the distal end comprises at least one aperture for receiving urine from the bladder; and
    a sleeve having a length, a width, and a size configured to receive the conduit, and wherein the sleeve surrounds substantially the entire length of the conduit;
    wherein the conduit and the sleeve are arranged in a helical coil, and wherein the shape of the helical coil is maintained by portions of the sleeve being releasably fixed together along at least a portion of the length of the sleeve.

2. The packaged urinary catheter according to claim 1, wherein a first cap seals a proximal end of the sleeve, and a second cap seals a distal end of the sleeve.

3. The packaged urinary catheter according to claim 2, wherein at least one of the first and second caps comprises a gripping feature configured to be grasped by a patient or user of the packaged urinary catheter.

4. The packaged urinary catheter according to claim 3, wherein the gripping feature is sized and shaped to receive a finger therethrough.

5. The packaged urinary catheter according to claim 2, wherein the packaged urinary catheter is released from the helical coil configuration by grasping the first and second caps, and urging the caps in substantially different directions.

6. The packaged urinary catheter according to claim 1, wherein portions of the sleeve are releasably fixed together by a perforated section along a length of the sleeve.

7. The packaged urinary catheter according to claim 1, wherein a lubricating material is contained within the sleeve.

8. The packaged urinary catheter according to claim 7, wherein the lubricating material is chosen from water, a hydrogel, and a vapor.

9. The packaged urinary catheter according to claim 1, wherein at least a portion of the outer surface of the conduit is hydrophilic.

10. The packaged urinary catheter according to claim 1, wherein the sleeve is constructed from two blanks of material that are joined at edges of the two blanks of material.

11. The packaged urinary catheter according to claim 1, wherein the sleeve is constructed from a foil material or a film.

12. A packaged urinary catheter, comprising:
   a synthetic polyisoprene conduit having a proximal end and a distal end, wherein the distal end comprises at least one aperture for receiving urine from the bladder; and
   a sleeve having a length, and a width, and a size configured to receive the conduit, and wherein the sleeve surrounds substantially the entire length of the conduit;
   wherein the conduit and the sleeve are arranged in a helical coil, and wherein the shape of the helical coil is maintained by portions of the sleeve being releasably fixed together along at least a portion of the length of the sleeve.

13. The packaged urinary catheter according to claim 12, wherein a first cap seals a proximal end of the sleeve, and a second cap seals a distal end of the sleeve.

14. The packaged urinary catheter according to claim 13, wherein at least one of the first and second caps comprises a gripping feature configured to be grasped by a patient or user of the packaged urinary catheter.

15. The packaged urinary catheter according to claim 14, wherein the gripping feature is sized and shaped to receive a finger therethrough.

16. The packaged urinary catheter according to claim 14, wherein the first and second caps are disposed outside the sleeve.

17. The packaged urinary catheter according to claim 16, wherein the packaged urinary catheter is released from the helical coil configuration by grasping the first and second caps, and urging the caps in substantially different directions.

18. The packaged urinary catheter according to claim 12, wherein a lubricating material is contained within the sleeve.

19. The packaged urinary catheter according to claim 18, wherein the lubricating material is chosen from water, a hydrogel, and a vapor.

20. The packaged urinary catheter according to claim 12, wherein at least a portion of the outer surface of the conduit is hydrophilic.

\* \* \* \* \*